United States Patent [19]

Donahoe et al.

[11] Patent Number: 5,011,687
[45] Date of Patent: Apr. 30, 1991

[54] PURIFIED MULLERIAN INHIBITING SUBSTANCE AND PROCESS FOR TREATING HUMAN OVARIAN CANCER CELLS

[75] Inventors: Patricia K. Donahoe, Weston; David A. Swann, Lexington, both of Mass.

[73] Assignee: The General Hospital Corporation, Boston, Mass.

[21] Appl. No.: 792,233

[22] Filed: Oct. 29, 1985

Related U.S. Application Data

[63] Continuation of Ser. No. 620,546, Jun. 18, 1984, abandoned, which is a continuation of Ser. No. 303,516, Sep. 18, 1981, abandoned, which is a continuation of Ser. No. 71,316, Aug. 30, 1979, abandoned.

[51] Int. Cl.$^5$ ............................................. A61K 35/48
[52] U.S. Cl. ........................................ 424/559; 514/8; 530/395; 530/397
[58] Field of Search ......................................... 424/105

[56] References Cited

PUBLICATIONS

Hakala and Rustum, Methods in Cancer Research, XVI:247 (1979).
National Cancer Institute Monograph, 55 (1980).
Cowan and Van Hoff, Cancer Chemotherapy, 1, (1983).
Tanneberger et al., Cancer Chemotherapy and Selective Drug Development (1984).
Salmon, Human Tumor Cloning, 499-508 (1984).
Rosenwaks et al., Abstract 174, 65th Annual Meeting, The Endocrine Society, Jun. 8, 1983.
Fuller et al., Gynecologic Oncology, "Mullerian Inhibiting Substance Inhibition of a Human Endometrial Carcinoma Cell Line Xenografted in Nude Mice," 1984 (preprint).
Donahoe et al., Annals of Surgery, 194: 472-480 (Oct., 1981); Fuller, Jr. et al., Gynceologic Oncology, 17: 124-132 (1984).
Swann, D. A., Donahoe, P. K. et al., Developmental Biology, vol. 69:73 (1979).
Donahoe, P. K. et al., Biology of Reproduction, 16:238-243 (1977).
Josso, N. et al., Biology of Reproduction, 13:163-167 (1975?).
Josso, N., J. Clin. Endocrinology, 34:265-270 (1972).
Picard, J. Y., and Josso, N., Biomedicine 25:147-150 (1976).

Primary Examiner—Jerome D. Goldberg
Attorney, Agent, or Firm—Saidman, Sterne, Kessler & Goldstein

[57] ABSTRACT

Purified Mullerian inhibiting substance (MIS) is obtained from testicular tissue by extraction, density gradient sedimentation and chromatography. The purified MIS has selective activity for inhibiting the growth of human ovarian cancer cells.

2 Claims, 2 Drawing Sheets

PURIFIED MULLERIAN INHIBITING SUBSTANCE AND PROCESS FOR TREATING HUMAN OVARIAN CANCER CELLS

The present invention is a continuation of application Ser. No. 620,546, filed June 18, 1984, (now abandoned) which is a continuation of application Ser. No. 303,516, filed Sept. 18, 1981, (now abandoned) which is a continuation of application Ser. No. 071,316, filed Aug. 30, 1979, (now abandoned).

BACKGROUND OF THE INVENTION

This invention relates to a method and composition for inhibiting of the growth of ovarian cancer cells and tumors.

The Mullerian duct in females develop into the uterus, fallopian tube and upper vagina.

Mullerian inhibiting substance (MIS) is a testicular product which initiates regression of the Mullerian duct in the male embryo of many mammalian species including rabbit, rat, calf and humans during the middle third of gestation and causes the Mullerian duct in the male to degenerate irreversibly.

MIS is interspecific so that its activity can be tested on the Mullerian ducts of fetal species other than the species of derivation.

Prior to the present invention, MIS has been isolated by incubating the cells of animal fetal testes in an organic culture. Thereafter, the medium is harvested and the active MIS containing fraction is isolated by standard techniques such as by centrifugation and chromatography. While the material obtained by this process contains active MIS, its use in treating animal cells is limited because it is not sufficiently pure. In addition, prior to the present invention, MIS had no known use other than the activity it exhibited in regression of Mullerian duct growth. It would be desirable to provide a method for obtaining MIS in sufficiently pure form so that it can be utilized to determine its effect on animal cells such as ovarian cancer cells. In addition, it would be desirable to provide a relatively pure MIS-containing composition to determine its effect on animal ovarian cancer cells in a selective manner without an undesirable toxic effect on normal cells.

SUMMARY OF THE INVENTION

This invention provides a process for inhibiting the growth of ovarian cancer cells in the selective manner by exposing the ovarian cancer cells to a purified form of Mullerian inhibiting substance (MIS). The purified MIS is obtained from testicular tissue by direct extraction followed by purification including centrifugation and fractionation to obtain a purified form of MIS. The purified form of MIS then is administered to ovarian cancer cells in order to inhibit their growth.

DESCRIPTION OF SPECIFIC EMBODIMENTS

Figure 1:
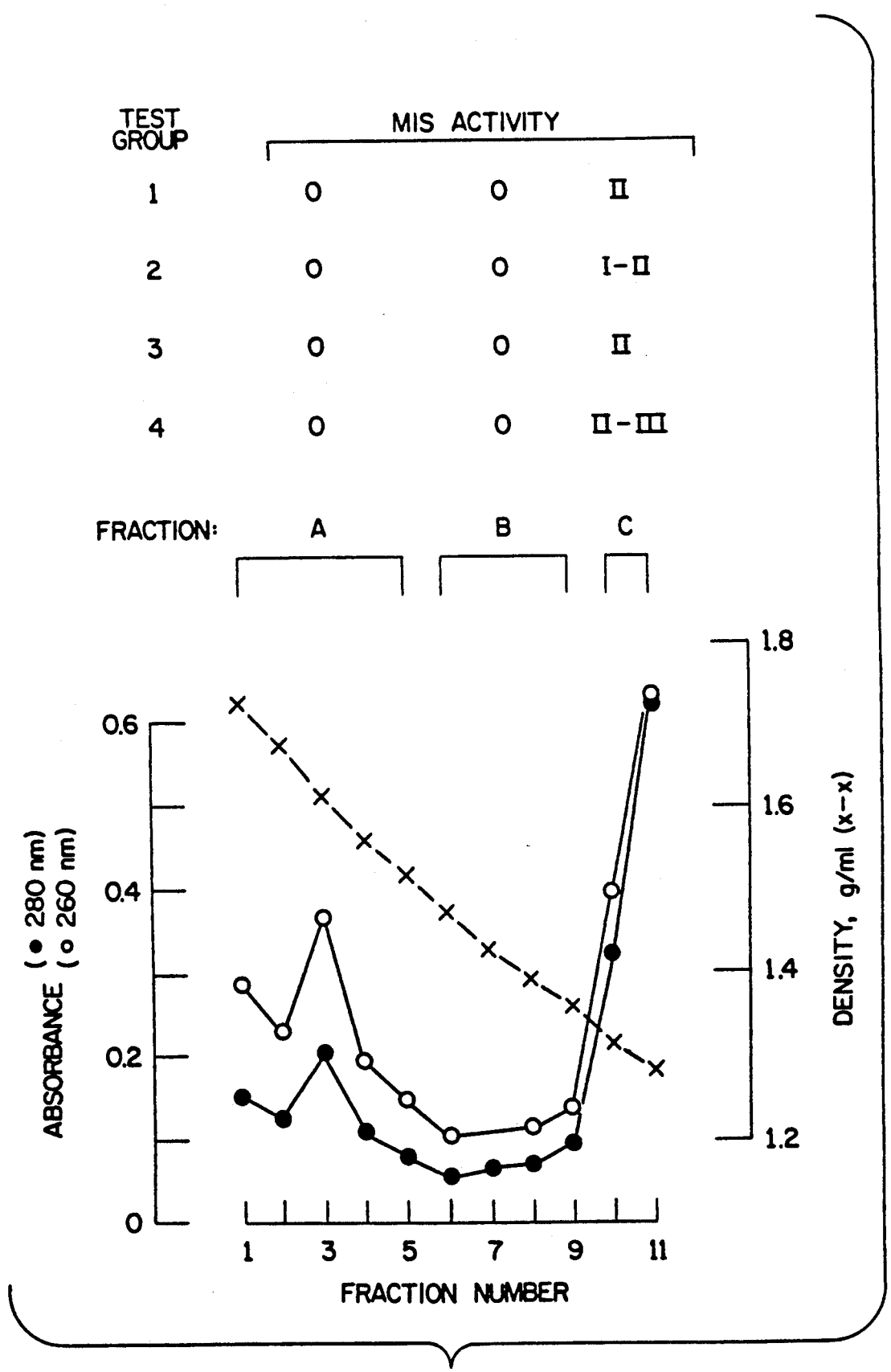

The present invention is based upon the discovery that MIS in a purified form is capable of inhibiting the growth of ovarian cancer cells. The purified compositions of this invention are obtained from testicular tissue. In order to be effective against ovarian cancer cells on a selected basis, the MIS should be purified to obtain at least about 0.5 mgm per gram of starting material and so that it has an activity of at least about 1 as measured by the Mullerian regression organ culture assay described below. If the MIS does not have this purity and activity level, it will not be effective against ovarian cancer cells on a selective basis since the material will be toxic also to normal cells to an undesirable extent. The major component in the biologically active fraction is a glycoprotein with a molecular weight of about 70,000 daltons.

Carbohydrate analysis shows that the carbohydrate portion of the active fraction comprises primarily mannose, galactose, glucosamine and N-acetylneuraminic acid while the peptide portion comprises between about 80 and 90 weight percent amino acids.

The MIS is obtained by excising testicular tissue from the newborn animals and thereafter mincing the tissue at a low temperature such as in ice in order to minimize or prevent degradation of the active MIS substance such as by release of protease. In this connection, it is preferred to effect the mincing of the tissue immediately after excising it from the animal also to minimize or prevent degradation of the active MIS material. The minced tissue then is suspended in an aqueous medium of a highly polar solvent such as guanidine chloride, guanidine bromide, high molar lithium chloride or other dissociative solvents which function to solubilize the protein and to extract the MIS from the tissue. Generally, the aqueous extraction solution has a pH between about 5 and 8.5. The resultant composition then is treated such as by centrifugation in order to separate the supernatant from the tissue. It is preferred to conduct this extraction step in the presence of a protease inhibitor such as benzamidine or the like. By utilizing the protease inhibitor, MIS degradation is minimized so that higher yields of the MIS are obtained.

The supernatant obtained from the centrifugation step comprises primarily proteins, DNA and RNA. In order to separate the active MIS rich fraction from the DNA and RNA, the supernatant is admixed with a material which effects density sedimentation of the larger DNA and RNA molecules. Such suitable materials include cesium chloride, cesium bromide, or other high density salts. The resultant composition then is centrifuged in order to stratify the MIS-rich fraction above the DNA and RNA within the container being centrifuged. The MIS-rich fraction then is separated from the DNA and RNA within the container such as by decantation or with a capillary tube as is conventional in the art. The fraction containing the MIS then is separated into its constituent parts by means of column chromatography. Representatives suitable materials which function to separate glycoproteins from other compositions in the MIS-rich fraction include agarose gel filtration materials. The fractions are eluted from the column by a salt solution as is conventional in the art and each fraction is tested for MIS activity. The MIS-active fractions then can be subjected to further chromatographic steps such as ion exchange chromatography in order to further purify the MIS.

The purified active MIS-rich fraction of this invention exhibits a profound effect for the inhibition of growth or for the selective destruction of transformed ovarian cells and tumors. The active MIS-rich fraction of this invention is administered to animal cells including human cells in tissue culture in a standard microcytotoxicity system to cancer cells derived from a human ovarian papillary cytodinoma carcinoma. Generally, the dosage of administration is at least about 100 picograms purified MIS-rich fraction per gram of excised whole tissue.

The following examples illustrate the present invention and are not intended to limit the same.

EXAMPLE I

This example illustrates the preparation of MIS in sufficiently pure form to afford its use for inhibiting the growth of ovarian cancer cells.

Newborn calf testes (1.5 g per testis) (Donahoe et al, Biol. of Reprod., 16, 238–243, 1977) were obtained from animals after death and dissected free of adjacent tissues at the slaughterhouse. This tissue (30 g) was diced rapidly by an automatic tissue chopper and suspended in 250 ml 1M guanidine hydrochloride, 0.05M Tris-HCl, pH 7.2, containing 0.005M benzamidine. The tissue suspended in the guanidine solution at 4° C. was transported to the laboratory and extracted for a further 48 hr at 4° C. with gentle stirring. The suspension was then centrifuged at 120,000 g for 1 hr at 4° C. in an ultracentrifuge. The tissue residue was discarded and the supernatant was then used for various fractionation procedures (Swann et al, Dev. Biol., 69, 73–84, 1979).

Fractionation Procedures

Density gradient sedimentation.

The density of the supernatant was adjusted to 1.50 g/ml by the addition of cesium chloride. This solution was then centrifuged at 120,000 g for 64 hr at 4° C. At the end of this time, fractions were obtained via a capillary tube inserted into the base of the centrifuge tube. The presence of nucleic acids and proteins in fractions was detected by measuring the absorbance at 260 and 280 nm, respectively. The density was determined by weighing known volumes of the fractions.

Gel filtration chromatography.

Aliquots of the protein fraction obtained by density gradient fractionation were fractionated on a Bio-Gel A-0.5M column (200×2 cm) eluted with 1M guanidine chloride, 0.05M Tris-HCl, pH 7.2. The column was operated at a flow rate of 20 ml/hr, and 11-ml fractions were collected. The column effluent was monitored for the presence of protein constituents by measuring the absorbance at 280 nm.

Chromatography on DEAE Bio-Gel.

Fractionation of aliquots of the protein fraction obtained by density gradient sedimentation or the fractions obtained by gel filtration chromatography was carried out using a column (20×2 cm) packed with DEAE Bio-Gel A-50 ion exchanger. Prior to application to the column, the sample was dialyzed overnight against water, for 8 hr against 1M NaCl, overnight against 0.15M NaCl, and for 48 hr against 0.05M Tris-HCl, pH 7.2. The column was operated at a flow rate of 20 ml/hr, and 10-ml fractions were obtained. The column eluate was monitored for the presence of peptide constituents by measuring the absorbance at 280 nm. After applying the sample, the column was washed with buffer until a steady baseline was obtained. The column was then eluted with a linear sodium chloride gradient which was monitored by conductivity measurement.

Chemical Analysis of Tissue Fractions

The protein content of fractions was determined by amino acid analysis (Moore et al, Ann. Chem. 30, 1185–1190, 1958). Glucosamine and galactosamine were also determined using the amino acid analyzer, following hydrolysis of samples with 6N HCl for 3 hr at 100° C. (Swann et al, Biochem., J., 161, 473–485, 1977). Other carbohydrate constituents were determined by gas-liquid chromatography after hydrolysis of samples with methanolic HCl and formation of the trimethylsilyl derivatives (Rheinhold, Methods Enzymol., 25, 244–249, 1972). The distribution of peptide constituents was determined by SDS gel electrophoresis (Furthmayr et al, Anal. Biochem., 41, 510–516, 1971.

Preparation of Antiserum to the Guanidine Extract Fraction

An antiserum ($AS_{GHCl}$) was prepared in rabbits against a guanidine extract supernatant fraction (described below) after dialysis of the extract against distilled water, 1M NaCl, and 0.15M NaCl. The supernatant obtained by centrifugation was lyophilized and mixed with complete Freund's adjuvant. New Zealand white rabbits were injected in the foot pads, and then intramuscular booster injections of incomplete Freund's adjuvant were given at 14, 23, 36 and 42 days. The animals were bled on Days 23, 57 and 65. Antisera from the fourth and fifth bleedings on Days 57 and 65 were used in these experiments. Antisera were absorbed repeatedly (9×) by the addition of lyophilized calf serum, followed by incubation at 4° C. for 16 hr and centrifugation, until no serum components were detected by double-diffusion analysis.

Pretreatment of Fractions Prior to Testing for MIS Activity

Aliquots of the guanidine extract supernatant or the gradient and column fractions to be tested in the in vitro organ culture system were dialyzed overnight against distilled water, for 8 hr against 1M sodium chloride, and for 48 hr against five changes of 0.15M NaCl, pH 7.2. The fractions were then concentrated on an Amicon ultrafilter fitted with a PM10 membrane to yield solutions of approximately 5 ml. Aliquots of the retained solution were mixed 1:1 with the culture medium used in the assay system, and sterilized by filtration under pressure through a 0.22-$\mu$m filter (Millipore). The concentration of samples in the test procedures corresponded to 0.3–1.5 g of testis/organ culture dish.

Organ Culture Assay System

The assay system used was described by Donahoe et al, J. Surg. Res., 23, 141–148, 1977 which is the Mullerian regression organ culture assay. The urogenital ridge was dissected from the 14-day female rat embryo and transferred to an organ culture dish (Falcon, 3010). Specimens were placed on stainless-steel grids coated with a thin layer of 2% agar and incubated for 72 hr at 37° C. in 5% $CO_2$ and 95% air over 2 ml of culture medium [CMRL 1066 containing 10% fetal calf serum, 1% penicillin (10,000 units/ml)] or a 1:1 mixture of culture medium and the supernatant or gradient fraction to be tested. The incubated tissue was then coated with a mixture of 2% agar and albumin at 44° C., fixed in buffered formaldehyde, dehydrated in ethanol, cleaned in xylene, and embedded in paraffin. Eight-micrometer serial sections were stained with hematoxylin and eosin for viewing by light microscopy. Sections from the cephalic end of the Mullerian duct were assigned a coded number and graded for regression (Donahoe et al, Biol. Reprod., 15, 329–334, 1976) on a scale of 0 to V. Five slides with six to eight sections per slide were read for each assay. A grade of activity was listed as the nearest whole number to the mean. A test group for the fractionation procedures represents at least 10 assays. If the mean fell midway between two numbers, then both numbers were listed. Grade 0 refers to no regression. The Mullerian duct, which is lined with columnar epithelial cells whose nuclei have a basilar orientation, has a widely patent lumen. Grade I is minimal regression. The duct is slightly smaller, and either the surrounding mesenchyme is condensed around the duct as seen in plastic sections or there is a clear area around the duct as seen in paraffin sections. Grade II refers to mild regression. The duct is smaller, and the mesenchymal condensation or the clear area around the duct is more pronounced. The nucleii of the shorter epithelial cells loose their basilar orientation. Grade III is moderate regression. The duct is very small and disorganized. The tip of the urogenital ridge develops poorly distal to the Wolffian duct. Grade IV is severe regression. The duct is replaced by a whorl of cells. Grade V refers to complete regression. No remnant of the duct can be detected. Positive tissue controls, using fetal testis, and negative tissue controls, where the Mullerian ducts were incubated alone or with muscle were included in each experiment. Mullerian ducts exposed to extracts from nontesticular tissue, to inactive testicular fractions, or to saline served as biochemical controls. Aliquots of all fractions were dialyzed against distilled water and freeze-dried, and protein content was measured.

MIS activity measurements were also performed using a guanidine extract supernatant fraction before and after absorption with normal rabbit serum or with an antibody to guanidine extract. The absorption was carried out three times by the addition of undiluted antiserum to the guanidine extract fraction, followed by incubation at 4° C. for 16 hr and centrifugation to remove the precipitate formed.

Preliminary experiments showed that extraction of calf testis with saline or urea solutions did not yield active extracts. Further experiments using 1M guanidine chloride solutions produced active extracts, but there was considerable variation in the degree of activity obtained and some were negative. Benzamidine (0.005M), a protease inhibitor, was then added to the guanidine solution used for the tissue extraction and consistent results were obtained. Aliquots in the range of 1 testis/plate or 0.5 testis/ml were added 1:1 with culture media. Attempts to concentrate further or to lyophilize resulted in a loss of biologic activity. The MIS activity in the extracts concentrated within this range varied from I to IV in different preparations.

Photomicrographs of the urogenital ridge of the 14.5-day female fetal rat after incubation showed with calf testis (Grade IV, positive), with calf muscle (Grade 0, negative), and with the guanidine chloride extract of newborn calf testis (Grade III). Parallel experiments carried out with adult bull testis and calf heart, two tissues that do not possess MIS activity in the organ culture test system, showed that the guanidine chloride extracts obtained from those tissues were also inactive.

Following extraction with guanidine chloride, the solutions obtained were always extremely viscous. These solutions had a high absorbance at 260 nm and presumably contained DNA. Dialysis of the tissue supernatant prior to testing in the organ culture assay system produced an insoluble precipitate. This precipitate was removed by centrifugation (120,000 g at 4° C.), and after extensive washing and resuspension in culture medium, portions of the resuspended precipitate were tested for MIS activity. Negative results were always obtained and the residue was therefore discarded.

Fractionation of whole tissue guanidine chloride extract by sedimentation in a cesium chloride density gradient yielded 11 fractions (FIG. 1). When these were tested for MIS activity (the result for each test group represents the nearest number to the mean of more than 10 assays), fraction 10 had minimal or no activity and fraction 11 possessed high activity. All other fractions were biologically inactive in the organ culture assay. Ion-exchange chromatography of protein fraction 11 obtained by density gradient sedimentation produced a series of fractions. In the example shown in FIG. 2b, seven fractions were obtained by pooling the column effluent.

As shown in FIG. 2, column chromatography of the protein fraction obtained by cesium chloride. (a) A column (200×2 cm) packed with Bio-Gel A.-0.5M was eluted with 1M guanidinium chloride, 0.05M Tris-HCl, pH 7.2, at a flow rate of 20 ml/hr, and 11-ml fractions were collected. $V_o$ indicates the elution position of blue dextran, and $V_1$ the elution position of $^3H_2O$. The protein fraction was prepared for chromatography by dialysis against the column eluents. Active fractions are shaded. (b) A column (20×2 cm) containing DEAE Bio-Gel equilibrated with 0.05M Tris-HCl, pH 7.2, was used. The gradient protein fraction was dialyzed against this buffer and then applied to the column, which was washed with the buffer until a stable baseline had been reestablished. The column was then eluted with a linear NaCl gradient, monitored by conductivity, at a flow rate of 16 ml/hr, and 8-ml fractions were obtained. The column effluents were monitored for protein constituents by measuring the absorbance at 280 nm. Fractions for testing in the organ culture assay system were obtained by pooling the column fractions as indicated. The results obtained for a series of preparations are shown. Each test group represents the nearest number to the mean of more than 10 assays. Active fractions are shaded in FIG. 2. Although essentially the same profile was obtained with different preparations, variations occurred in the resolution obtained between the constituents eluted by the gradient. Testing the pooled column effluent fractions for MIS activity, however, indicated that the consituents eluted between 0.15 and 0.20N NaCl possessed positive activity, while the other fractions were negative.

Figure 2A:
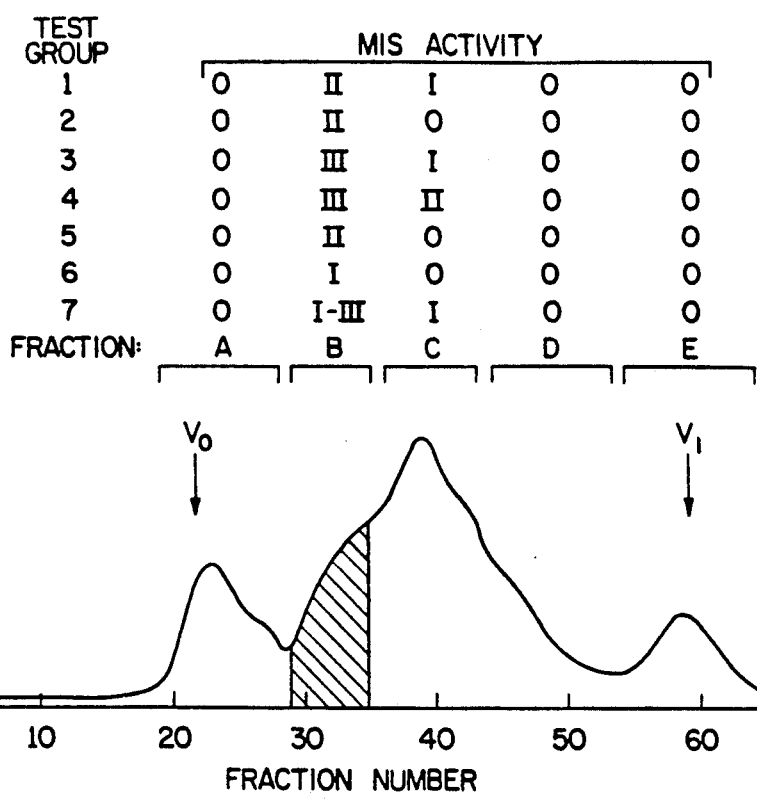
Figure 2B:
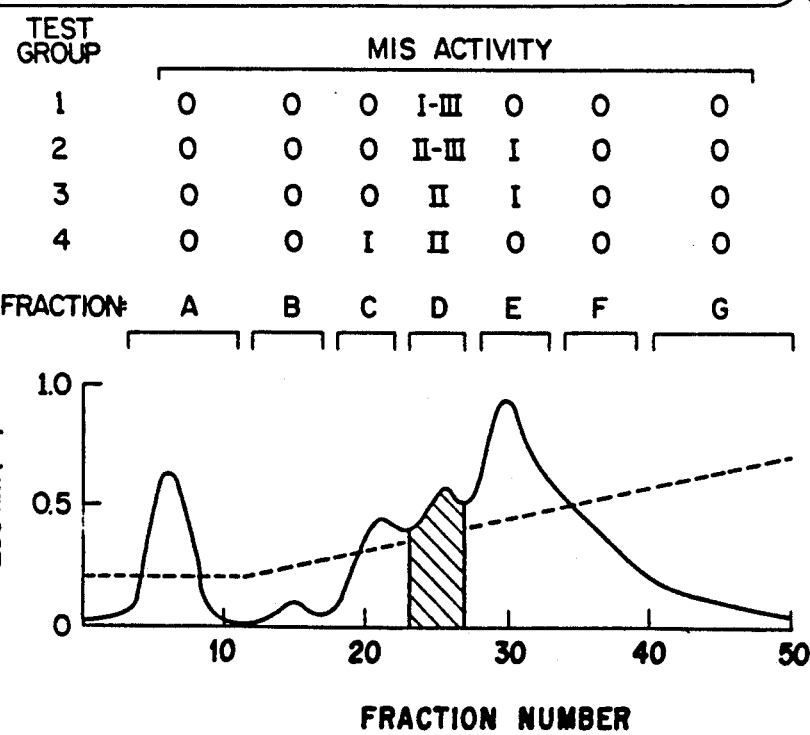

Gel filtration chromatography of the protein fraction obtained by the cesium chloride density gradient procedure (fraction 11, FIG. 1) on a Bio-Gel A-0.5M column (FIG. 2a) produced three major fractions: a void volume, a large heterogeneous peak eluted in the included volume, and a third peak eluted close to the total volume of the column. Based on the elution profile obtained, the column effluent fractions were pooled as indicated in FIG. 2a. Testing these fractions for MIS showed that constituents eluted with $K_{av}$ values between 0.19 and 0.38 (fraction B) were active. The other fractions were inactive.

Analysis of the active column fractions by disc gel electrophoresis showed the presence of several peptide constituents. The major constituent, with a mobility intermediate between those of collagen $\alpha$ chains and ovalbumin, stained with periodic acid-Schiff reagent, and is therefore a glycoprotein. Amino acid and carbohydrate analyses showed that active fractions obtained by gel chromatography contained between 85 and 89% (w/w) amino acids and 7% (w/w) carbohydrates (mannose, 1.5%; galactose, 4.5%; glucosamine, 1.0%; and N-acetylneuraminic acid, 2.0%). The amino acid analysis indicated that the major components in active fractions did not have an unusual amino acid composition.

Using undiluted antiserum ($AS_{GHCl}$) prepared in rabbits against a guanidine extract supernatant fraction, which had been absorbed nine times with fetal calf serum, up to four precipitate bands were detected in the active guanidine extract and column fractions. However, precipitate lines could not be detected against calf serum, indicating that the observed antigenic components present in the active fractions were derived from the testis. Precipitate bands were detected against an active fraction when the antiserum was serially diluted to 1:300.

The guanidine extract supernatant fraction exhibited Grade II regression of the Mullerian duct. Similar regression was also observed when extract fractions were absorbed with freeze-dried normal rabbit serum. When the samples were absorbed with the antiserum raised to a guanidine extract with Mullerian inhibiting substance activity ($AS_{GHCl}$), however, the MIS activity of the guanidine extract fraction was virtually eliminated.

EXAMPLE II

This example illustrates that active MIS obtained by the procedure set forth in Example I has significant cytotoxic activity against ovarian tumor. An ovarian tumor was surgically removed from a 56 year old woman in 1971 and was serially subcultured since then. Histologically, the tumor is described as a papillary serous cystadenocarcinoma that is moderately well differentiated. The epithelioid line doubles every 28 hours, has a near diploid karyotype, and can produce tumors with a histology similar to the original tumor when $10^4$ or more cells are heterotransplanted into the hamster check pouch by the procedure of Yamada, Keio, J. Med., 23, 57, 1974. This line has been serially subcultered in stationary monolayers at 37° C. in Eagle's minimum essential medium (MEM) containing 15 percent fetal calf serum, 1 percent penicillin (10,000 units/ml), and streptomycin (10,000 µg/ml). As control lines a human fibroblast strain derived from the foreskin of a 1-year old undergoing circumcision, and a glioblastoma (non-Mullerian duct tumor) line were used. The control lines were grown in stationary monolayers at 37° C. in F10 nutrient medium containing 10 percent fetal calf serum and 1 percent penicillin and streptomycin. All lines were free of mycoplasma.

By methods adapted from those of Wood and Morton, Science, 170, 1318, 1970, monolayers of the cell lines, after they approached confluency (3 days after a 1:2 subculture), were washed with $Ca^{2+}$- and $Mg^{2+}$-free Hanks balanced salt solution, dispersed with 0.25 percent trypsin-EDTA (Gibco), and counted in a hemocytometer. Appropriate dilutions for each cell line were made with either MEM or $F_{10}$ containing 20 percent fetal calf serum, and 300–400 cells were delivered to each well of a Falcon 3034 microtest plant in a 0.01-ml volume with a six-barrel Teresaki syringe. Plates were surrounded by moistened gauze, placed in a plastic box with the lid ajar and incubated at 37° C. in a humidified incubator with an atmosphere containing 5 percent $CO_2$ and 95 percent air. The following morning medium was blotted from the wells and replaced with new medium (0.01 ml per well). Testis fractions and controls were then added in 0.01-ml portions (total volume, 0.02 ml per well). After a 24 hour incubation period, the plates were washed and stained with Giemsa, and the adherent cells were counted on a projection screen. Six replicate wells were used for each test fraction. The microtest plates contained phosphate buffered saline (PBS) as a negative control, fractions from newborn calf heart (no Mullerian duct regression) as a tissue negative control, and fractions from newborn calf testes that were either inactive (biochemical negative controls) or active (test substance) in the organ culture assay obtained by the procedure of Example I. The counts of the 18 PBS control replicate wells were averaged and compared with the average of the six replicates of each fraction tested, and a cytotoxicity index [CI=(Control well counts−test well counts)/control well counts] was calculated separately for each plate. A CI greater than 0.25 differed significantly from the controls ($P<0.01$. Student's test). Mullerian duct regression activity was simultaneously determined for each test fraction, and the activity in an organ culture assay was correlated with the cytotoxicity assay on the human ovarian cancer cells.

Newborn calf testes were diced rapidly in an automatic tissue chopper, suspended in a 1M guanidine hydrochloride solution containing 5 mM benzamidine at 4° C., and sequentially purified (Table I).

Multiple-step dialysis and concentration back to an equivalent weight of the starting material was performed at each step, and all fractions were tested for biological activity in the organ culture assay for Mullerian duct regression. Aliquots of the biologically active and inactive fractions were stored at 80° C. or −196° C. for subsequent microcytotoxicity assay.

The urogenital ridge was dissected from a 14-day-old female rat embryo and transferred to agar-coated stainless steel grids in Falcon 3010 organ culture dishes. Specimens were incubated for 72 hours at 37° C. in 5 percent $CO_2$ and 95 percent air over 2 ml of culture medium [CMRI, 1066 containing 10 percent fetal calf serum, 1 percent penicillin (10,000 units/ml), and streptomycin (10,000 µg/ml), or containing a 1:1 mixture of culture medium and purified fractions from calf testis or heart extracts or PBS. The incubated tissue was then coated with a mixture of 2 percent agar and albumin at 44° C. and fixed and embedded in paraffin. Serial sections (8 µm) were stained with hematoxylin and eosin for viewing by light microscopy. Sections from the cephalic end of the Mullerian duct were assigned a coded number and graded for regression on a scale of 0 to 5 by two independent observers (Table 1). Grade 0 refers to no regression, grade 1, minimal, grade 2, mild, grade 3, moderate, grade 4, severe, and grade 5, complete regression, based on characteristic morphologic changes in the epithelial cells and surrounding mensenchyme.

As shown in Table 1, a significant CI (0.37, $P<0.01$) against the human ovarian carcinoma was obtained when the biologically active fraction 11, obtained by density gradient sedimentation of the guanidine extract, was applied to the cells in the microtest wells. Biologically active fraction B, obtained by column chromatography of fraction 11, had a significant cytotoxic index (CI—0.45, $P<0.01$), whereas gel chromatography fractions A and C, which were inactive in the organ culture assay, had an insignificant CI (0.24). A significant cytotoxic effect was not obtained when similar fractions from newborn calf heart were tested against the human ovarian carcinoma cells (HOC-21). Similarly, none of these fractions from nontesticular tissue demonstrated Mullerian duct regression in the organ culture assay. When gel chromatography fraction B from calf testis was tested in the miblast line or a ghoblastoma line, no significant cytotoxic effect was observed (Cl—0.01 and 0.11, respectively). A cytotoxic effect was not observed when biologically active fractions were applied against the human ovarian cancer line which had been subcultured for more than 3 days earlier. This effect also was not present when the plates were sparsely (less than 50 cells per well) or densely (greater than 100 cells per well) seeded.

Thus fractions isolated from newborn calf testes that demonstrated Mullerian duct regression in the organ culture assay of the 14-day-embryonic rat Mullerian duct also demonstrated a cytotoxic effect against a human ovarian carcinoma line, presumably of Mullerian duct nature. This same effect against the human ovarian cancer line was not observed with fractions lacking MIS biological activity in the organ culture system. Biologically active fractions had no effect against the non-Mullerian human glioblast or against a human fibroblast strain.

The cytotoxic response elicited by testis fractions that cause Mullerian duct regression in the embryo indicates that this tumor is, like embryonic tissue, responsive to fractions with MIS activity. The response also indicates that the interaction of these fractions with the tumor has led to loss of cell adherence and possibly cell death.

The cytotoxic effect was not observed unless synchrony of the cell cycle and the density of cell seeding were carefully controlled. Noncoercive partial synchrony of the cell cycle was obtained by subculture with a 1:2 division 3 days prior to and again at the time of harvesting and seeding the microtest plates, in each case just before confluency was reached. It has been shown that DNA synthesis (S phase), as measured by thymidine uptake, is maximal just before confluency.

Test fractions were added 20 hours later, coincident again with the S phase of the cell cycle, and allowed to incubate for a subsequent 24 hours. Preliminary experiments demonstrated that cells subcultured more than 5 days before seeding, when thymidine uptake falls to negligible levels failed to respond to biologically active MIS fractions. Presumably, cells in the S phase are more responsive to MIS. This finding correlates with previous observations with the electron microscope of active, euchromatic nuclei occuring in all Mullerian duct epithelial cells during the initial phases of regression. Cells seeded at densities of greater than 100 cells per well failed to respond to Mullerian Inhibiting Substance. The effect of cell density on MIS responsiveness may be related (i) to diminished surface receptors for the cytotoxic material, since a dense population might cover receptor sites that would become more exposed if the cells were allowed to spread more fully on a monolayer, or (ii) to the uncoupling of DNA synthesis usually seen with cell adherence and spreading. The results in Table 1 were obtained with newborn calf testis or heart fragments extracted with guanidine, subjected to density gradient sedimentation (DGS) in CsCl, (1.5 g/ml), ultrafiltration (Amicon PM30), and then gel chromatography (GC) (fractions A, B, and C) in a 200-by 2.6-cm column packed with Bio-Rad A-5M Biogel. Dialyzed and concentrated fractions were then assayed for Mullerian duct regression. Fractions with positive and negative biological activity were mixed with medium and added to wells of the microtest plates in which cells of appropriate density were synchronized in the S phrase of the cell cycle.

TABLE I

| Sample | Ovarian carcinoma Average number cells per well | Cl | Skin fibroblasts Average number cells per well | Cl | Blioblastoma Average number cells per well | Cl | Organ culture regression grades |
|---|---|---|---|---|---|---|---|
| | | | TESTIS | | | | |
| DGS fraction 11 (1:1 dilution) | 54.0 | 0.37* | 60.0 | −0.01 | | | 2 to 3+ |
| CMRL | 91.2 | 0.06 | 68.3 | 0.15 | | | 0 |
| PBS | 83.7 | | 61.2 | | | | |
| DGS fraction 11 (1:3 dilution) | 65.3 | 0.24 | 54.3 | 0.09 | | | 2 to 3+ |
| CMRL | 91.8 | −0.07 | 70.7 | −0.19 | | | 0 |
| PBS | 84.8 | | 58.3 | | | | 0 |
| GC fraction A | 52.0 | 0.24 | | | | | 0 |
| GC fraction B | 37.7 | 0.45* | | | | | 2+ |
| GC fraction C | 51.6 | 0.24 | | | | | 0 |
| PBS | 66.5 | | | | | | 0 |
| | | | HEART | | | | |
| GC fraction B | 66.0 | 0.03 | | | | | 0 |
| | | | TESTIS | | | | |
| GC fraction B | 68.3 | 0.32* | 75.5 | 0.01 | | | 2+ |
| PBS | 100.5 | | 71.5 | | | | 0 |
| | | | HEART | | | | |
| GC fraction B | 85.0 | 0.16 | 82.2 | −0.08 | | | 0 |
| | | | TESTIS | | | | |
| DGS fraction 11 | | | | | 104.0 | 0.05 | 3 to 4+ |
| GC fraction B | | | | | 116.0 | −0.05 | 0 |
| | | | HEART | | | | |
| GC fraction B | | | | | 119.0 | −0.08 | 0 |
| PBS | | | | | 108.8 | | 0 |
| | | | TESTIS | | | | |
| GC fraction B | | | | | 122.2 | −0.11 | 2 to 4 + |

*P < .01

We claim:

1. A purified form of Mullerian Inhibiting Substance (MIS) which, when isolated from testicular tissue comprises a glycoprotein having the following characteristics:
   (a) an activity of at least 1 as measured by the Mullerian regression organ culture assay, which is substantially free of testicular tissue and of proteinaceous material capable of degrading said MIS;
   (b) a cytotoxicity index of greater than 0.25 towards synchronously growing cells in a cell culture of a human ovarian papillary serous cystadenocarcinoma, when said cell culture is populated at a density between 50 and 100 cells per well, but showing no statistically significant cytotoxicity towards non-Mullerian human gliobastomas or against human fibroblasts;
   (c) molecular weight about 70,000 daltons;
   (d) carbohydrate fraction: mannose, galactose, glucasamine, and N-acetylneuraminic acid; and
   (e) peptide fraction: 80–90 weight percent amino acids.

2. A method for inhibiting the growth of human ovarian cancer cells which comprises administering to said cells Mullerian Inhibiting Substance in an amount effective to inhibit the growth of said cells.

* * * * *